United States Patent
Fatemi et al.

(10) Patent No.: US 11,234,673 B2
(45) Date of Patent: Feb. 1, 2022

(54) AUTOMATED TIME-DOMAIN DETERMINATION OF TISSUE VISCOELASTICITY IN A SUB-HERTZ FREQUENCY RANGE

(71) Applicant: Mayo Foundation for Medical Education and Research, Rochester, MN (US)

(72) Inventors: Mostafa Fatemi, Rochester, MN (US); Mahdi Bayat, Rochester, MN (US); Alireza Nabavizadehrafsanjani, Bronx, NY (US); Azra Alizad, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 564 days.

(21) Appl. No.: 16/167,791

(22) Filed: Oct. 23, 2018

(65) Prior Publication Data

US 2019/0159751 A1 May 30, 2019

Related U.S. Application Data

(60) Provisional application No. 62/575,638, filed on Oct. 23, 2017.

(51) Int. Cl.
*A61B 8/00* (2006.01)
*A61B 8/08* (2006.01)

(52) U.S. Cl.
CPC .......... *A61B 8/085* (2013.01); *A61B 8/0825* (2013.01); *A61B 8/4209* (2013.01); *A61B 8/485* (2013.01);

(Continued)

(58) Field of Classification Search
CPC ...... G16H 50/30; A61B 8/085; A61B 8/5223; A61B 8/4209; A61B 8/485; A61B 8/0825;

(Continued)

(56) References Cited

U.S. PATENT DOCUMENTS

| 2014/0288424 A1* | 9/2014 | Mukdadi | A61B 8/483 |
| | | | 600/438 |
| 2014/0296709 A1* | 10/2014 | Fatemi | A61B 8/5223 |
| | | | 600/438 |
| 2019/0175140 A1* | 6/2019 | Fatemi | A61B 8/5207 |

OTHER PUBLICATIONS

Wells, P. N. T. et al., "Medical ultrasound: imaging of soft tissue strain and elasticity," Journal of The Royal Society Interface, Jun. 16, 2011, vol. 8, No. 64, pp. 1521-1549.

(Continued)

*Primary Examiner* — Joel Lamprecht
(74) *Attorney, Agent, or Firm* — Quarles & Brady LLP; Yakov S. Sidorin

(57) ABSTRACT

Methodology, with a programmable-processor imaging system, for control and determination of breast lesion viscoelastic properties with the use of a creep-like test. Two dimensional reconstruction maps are used for different parameters of a linear viscoelastic model. Description of different aspects of the test used on live subjects and suitability of a 1-D inversion model in capturing different viscoelasticity parameters. An automated methodology for the selection of a region of interest derived only from the appearance of the breast lesion on pre-compressed B-mode images. Based on the ROI and estimated viscoelasticity parameters, contrast values are determined that facilitate the enhanced differentiation of breast mass. Employing the methodology in a large group of patients provides better understanding of variations of different viscoelasticity parameters in different types of (Continued)

breast lesion and helps to identify new biomarkers for enhanced differentiation of benign from malignant cases.

5 Claims, 16 Drawing Sheets

(52) U.S. Cl.
CPC ............ *A61B 8/5223* (2013.01); *A61B 8/403* (2013.01); *A61B 8/4281* (2013.01); *A61B 8/463* (2013.01); *A61B 8/466* (2013.01); *A61B 8/5253* (2013.01)

(58) Field of Classification Search
CPC ..... A61B 8/403; A61B 8/4281; A61B 8/5253; A61B 8/463; A61B 8/466
See application file for complete search history.

(56) References Cited

OTHER PUBLICATIONS

Qui, Y. et al., "Ultrasonic Viscoelasticity Imaging of Nonpalpable Breast Tumors: Preliminary Results," Academic Radiology, Dec. 2008, vol. 15, No. 12, pp. 1526-1533.

Sridhar, M. et al., "Ultrasonic measurements of breast viscoelasticity," NIH Public Access Author Manuscript, published in final edited form as: Medical Physics, Dec. 2007, vol. 34, No. 12, pp. 4757-4767.

Parker, K. J. et al., "A unified view of imaging the elastic properties of tissue," The Journal of Acoustical Society of America, May 2005, vol. 117, No. 5, pp. 2705-2712.

\* cited by examiner

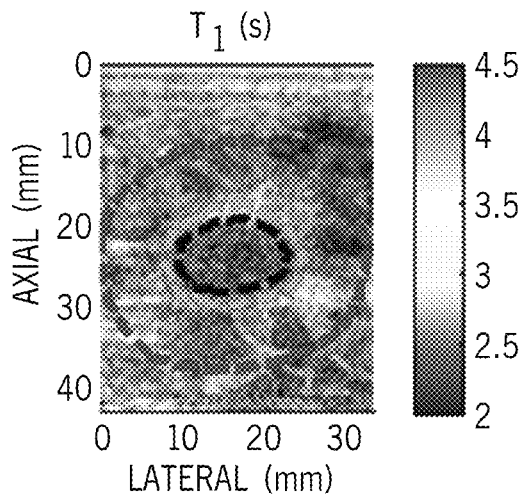
FIG. 7G
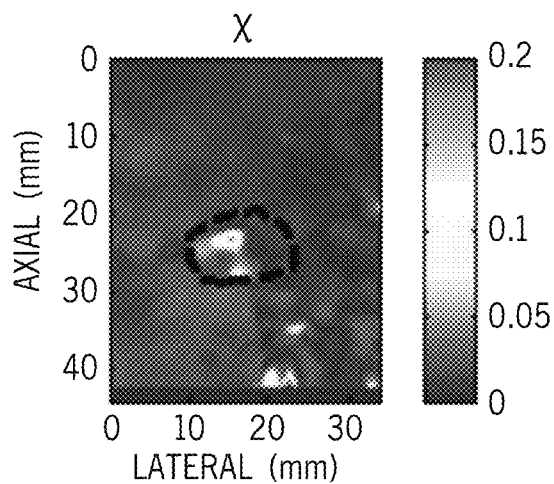
FIG. 7H
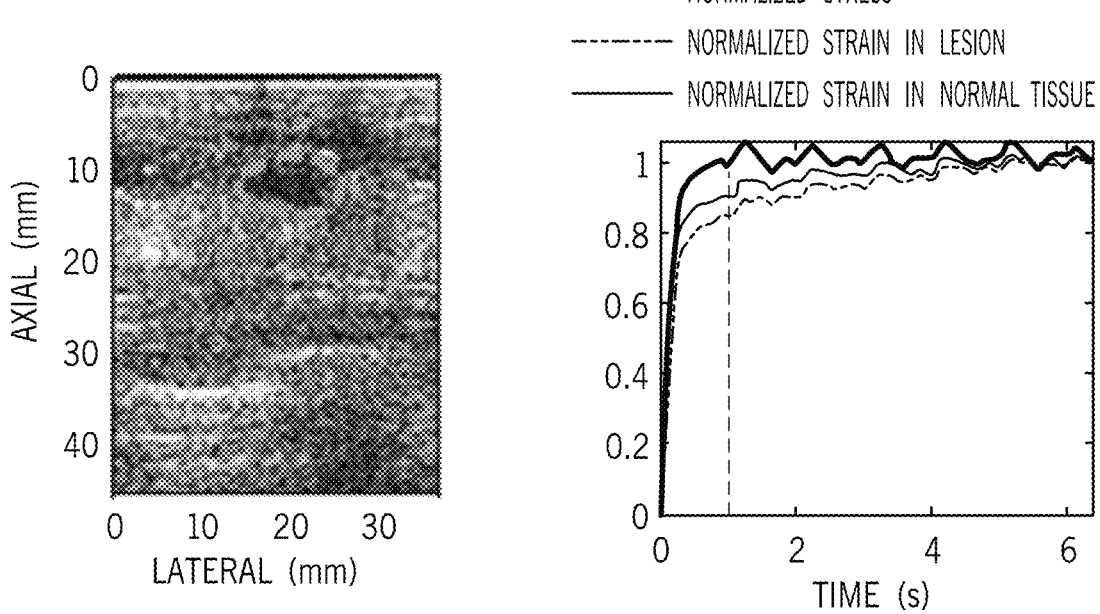
FIG. 7I
FIG. 7J

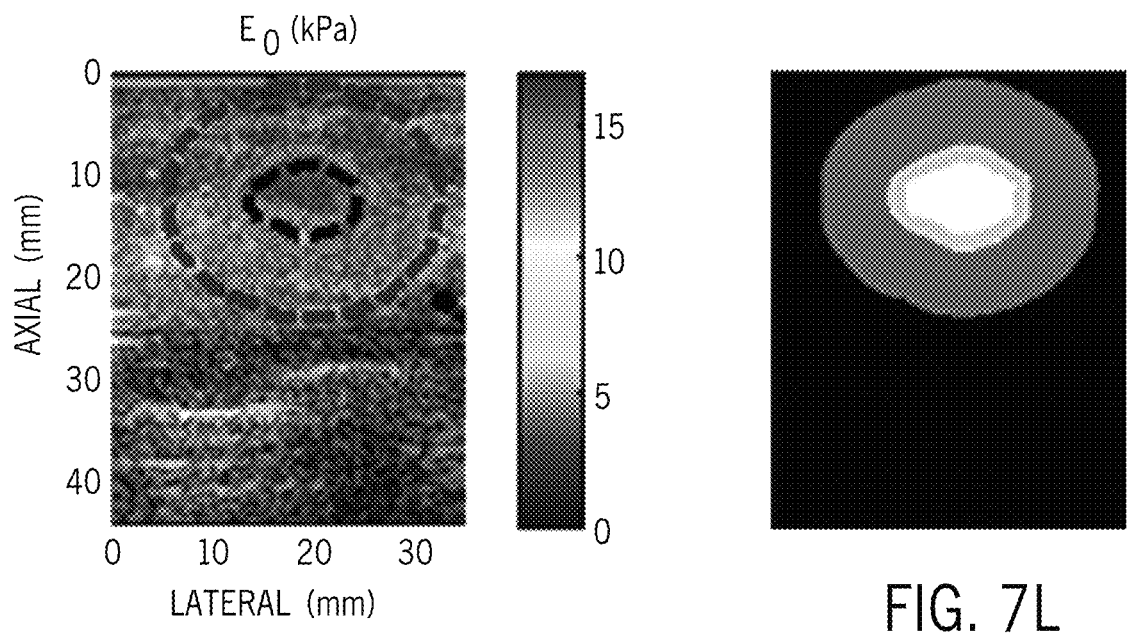
FIG. 7K
FIG. 7L
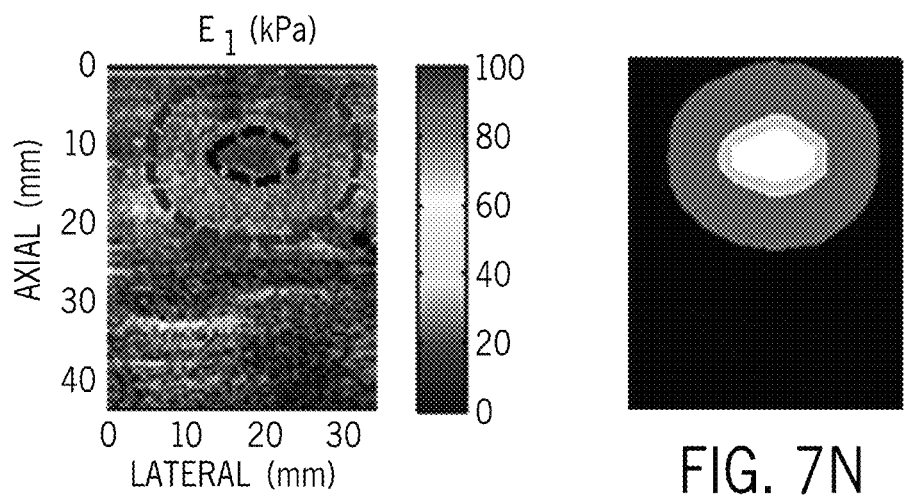
FIG. 7M
FIG. 7N

Table 1: viscoelastic parameters estimated from the simulation axial stain data from different models

|  | Model parameters | Uniform block | Model3-1 | Model1-3 |
|---|---|---|---|---|
| Material 1 | $E_0 = 45 kPa$<br>$E_1 = 450 kPa$<br>$T_1 = 1s$ | $E_0 = 108 \pm 152.28 kPa$<br>$E_1 = 602.61 \pm 81.18\ kPa$<br>$T_1 = 1.01 \pm 0.02s$ | $E_0 = 65.05 \pm 8.71$ kPa<br>$E_1 = 621.52 \pm 86.78$ kPa<br>$T_1 = 1.10 \pm 0.07s$ | $E_0 = 65.39 \pm 8.75$ kPa<br>$E_1 = 562.73 \pm 78.60$<br>$T_1 = 2.16 \pm 0.07$ s |
| Material 2 | $E_0 = 45 kPa$<br>$E_1 = 450 kPa$<br>$T_1 = 3s$ | $E_0 = 105.66 \pm 142.90 kPa$<br>$E_1 = 537.66 \pm 70.55$ kPa<br>$T_1 = 3.0215 \pm 0.22s$ | $E_0 = 49.12 \pm 1.60$ kPa<br>$E_1 = 459.56 \pm 14.39 kPa$<br>$T_1 = 1.77 \pm 0.07s$ | $E_0 = 49.17 \pm 1.59$ kPa<br>$E_1 = 450.06 \pm 14.30$ kPa<br>$T_1 = 2.91 \pm 0.10$ s |

FIG. 11

AUTOMATED TIME-DOMAIN DETERMINATION OF TISSUE VISCOELASTICITY IN A SUB-HERTZ FREQUENCY RANGE

CROSS-REFERENCE TO RELATED APPLICATIONS

This patent application claims priority from and benefit of the U.S. Provisional Patent Application No. 62/535,638 filed on Oct. 23, 2017 and titled "Automated Time-Domains Analysis of Tissue Viscoelasticity in a Sub-Hertz Frequency Range". The disclosure of this provisional patent application is incorporated herein by reference.

STATEMENT OF FEDERALLY-SPONSORED RESEARCH AND DEVELOPMENT

This invention was made with government support under CA168575 awarded by the National Institutes of Health. The government has certain rights in the invention.

TECHNICAL FIELD

This invention pertains to a methodology for assessing viscoelasticity of a biological tissue and, in particular, to a system for ultrasound imaging (of a compressed target object) that, in operation, controls the ramp time of compression of the object in temporal synchronization of a compression device with an imaging portion of the system and facilitates the determination of a spatial profile of a strain response of the target object as a function of time and/or a viscoelastic retardation time that characterizes the object.

BACKGROUND

Pathologic changes in tissues can manifest as changes in mechanical properties of the tissues. In non-invasive quasi-static strain elastography, an axial compression is applied to the tissue, and tissue deformation is visualized by analyzing the pre-compression and post-compression ultrasonic data. In maps, constructed based on such data and referred to as "elastograms", softer parts of the tissue show higher levels of deformation (strain) as compared to the stiffer parts. In breast tissue, while analysis of the elasticity alone can predict architectural changes in tissue to some extent, the complexity of tissue biomechanics requires a more comprehensive model to predict a wider range of pathologies. In breast tumors, particularly, finding a mechanical property that not only shows sensitivity to malignancy, but also shows sensitivity to benign changes can be extremely beneficial as it can potentially enhance diagnosis specificity which in turn may reduce a significant number of unnecessary, painful and costly biopsies.

Recent studies have aimed at extending the notion of elastography to more comprehensive models that account for the biphasic nature of the tissue. These works have resulted in models based on viscoelasticity, poroelasticity, and poroviscoelasticity, and have shown that two major components play important roles in governing tissue deformation under external compression: a) the drained matrix viscoelasticity (which is mostly defined by the fiber density, orientation and cross-linking density), and b) the interstitial fluid motion that creates retardation in the deformation rate via frictional forces. However, a comprehensive methodology that describes tissue biomechanics at a wide range of frequencies is still desired. For example, the studies conducted with the use of magnetic resonant elastography (MRE) suggestsed that a single model simply cannot simultaneously explain tissue behavior in different frequency ranges. Hence, a unified approach to separate the dynamics of the two phases (i.e. a viscoelastic deformable solid response and a hydraulic fluid motion) in tissue-like materials remains an open problem, as was recognized by, for example, M. Galli et al. (*Journal of Materials Research*, vol. 24, pp. 973-979, 2009/003/001 2009) and M. L. Oyen (*Current Opinion in Solid State and Materials Science*, vol. 19, pp. 317-323, 2015). To address these shortcoming, alternative approaches (which describe tissue deformation as purely poroelastic or purely viscoelastic solids) are favored.

Unlike quasi-static strain elastography, which relies only on pre- and post-deformation states of the tissue, these alternative methods require continuous observation of the tissue response under an external stimulation. For example, methods based on poroelasticity imaging require observation of the tissue dynamic deformation during hundreds of seconds while a constant surface compression is maintained. The methods based on viscoelastic models, on the other hand, have shown to predict mechanical properties in shorter time scales, which is more favorable for in vivo applications. Tissue deformations at these time scales reside in a frequency range of less than 1 Hz. Stress-relaxation and creep-compliance tests are two standard mechanical testing methods suitable for this range of frequency. While stress-relaxation may not be feasible for in vivo scenarios (due to lack of accurate estimate of the stress distribution), with appropriate assumptions creep-like tests can be performed with the help of a force-control mechanism that mimics a ramp-and-hold stress excitation and monitoring internal strain field via ultrasonic strain tracking algorithms.

While malignant and benign masses may present different viscoelastic characteristic as a result of a creep-like test with limited force feedback information, the added noise (caused by manual operation, lack of an accurate estimate of the excreted force (to ensure operation in linear regime and maintaining a constant force), and dependency of the interpretation of imaging contrasts based on different viscoelastic parameters on the operator limits the utility and reproducibility of such method for patient studies.

SUMMARY

Embodiments of the invention provide a system for ultrasound imaging of a compressed target object. Such system includes a compression device configured to apply a compression force to the target object (in particular, by increasing the compression force with a constant ramp time from an initial value to the final predetermined value, and, once the final predetermined value has been reached, maintaining the compression force applied at a substantially constant level). The system also includes an ultrasound probe with an ultrasound transducer. (Here, the probe is mechanically coupled with the compression device and configured to receive an ultrasound wave from the target object in a time-window, during which the compression device holds the ultrasound probe in contact with the target object and while the compression force is being applied to the target object). The system additionally includes an ultrasound imaging system cooperated with the ultrasound probe and structured to record a sequence of ultrasound image data frames during the time-window, wherein the ultrasound image data frames represent a region of interest (ROI) of said target object; and a compression device controller, operably cooperated with the compression device and including electronic circuitry programmed (i) to set and control the ramp time, and (ii) to synchronize an operation of the compression device with an operation of the ultrasound imaging system. Finally, the system contains a data-processing unit configured to receive signal outputs produced at least by the ultrasound imaging system and the compression device controller (such signal outputs representing the target object imaged with the ultrasound imaging probe while being compressed by the compression device) and to determine, based on the signal outputs, a spatial profile of a strain response of the target object to the compression force as a function of (i) time, and (ii) a viscoelastic retardation time characterizing the target object. In a specific implementation, the system for ultrasound imaging is configured to determine a two-dimensional distribution of first and second viscoelastic parameters $E_0$, $E_1$ (characterizing an area of the target object, to which the compression force has been applied) based on the spatial profile and according to $$\hat{E}_0(m, n) = \frac{\sigma_0}{\epsilon_{m,n}(T_r)},$$

$$(\hat{E}_1(m, n), \hat{T}_1(m, n)) = \underset{(E_1, T_1)}{\operatorname{argmin}} \left\| \frac{\sigma_0}{E_1}\left(1 - e^{-\frac{t}{T_1}}\right) - (\epsilon_{m,n}(t) - \epsilon_{m,n}(T_r)) \right\|^2,$$

$$t > T_r.$$

Here, $\sigma_0$ is a maximum value of stress caused by the compression force, $T_r$ is the ramp time, $T_1$ is the viscoelastic retardation time, $\epsilon_{m,n}(t)$ and $\hat{\epsilon}_{m,n}(t)$ are a two-dimensional distribution of a measured strain profile and a two-dimensional distribution of a fitted strain profile respectively; and ‖.‖ indicates the Euclidian norm.

Embodiments of the invention additionally provide a method for ultrasound imaging of a compressed target object. The method includes the following steps: (i) with an automated compression device, applying a compression force to the target object while varying the compression force from an initial value to the final predetermined value and, once the final predetermined value has been reached, maintaining such compression force applied at a substantially constant level; (ii) receiving an ultrasound wave from the target object, insonated with an ultrasound transducer of the ultrasound probe during a period of time while the target object is compressed with the compression force; (iii) with an ultrasound imaging system, recording a sequence of ultrasound image data frames during the period of time, based on data from said ultrasound wave, wherein the ultrasound image data frames represent a region of interest (ROI) of the target object; and (iv) with a programmable computer processor, operably cooperated with at least the compression device and the ultrasound imaging system, determining a spatial profile of local strain across the target object, caused by the step of applying the compression force, as a function of time and as a function of a viscoelastic retardation time characterizing the target object. In one embodiment, the step of varying the compression force at a constant rate with a pre-determined ramp time; and the step of applying includes (a) setting and controlling the constant rate, and (b) synchronizing an operation of the automated compression device with an operation of the ultrasound imaging system. Alternatively or in addition, the method may include a step of determining a viscoelastic parameter, characterizing the target object, as a function of time based at least on the constant rate.

BRIEF DESCRIPTION OF THE DRAWINGS

The invention will be more fully understood by referring to the following Detailed Description in conjunction with the generally-not-to-scale Drawings, in which similar elements are indicated with similar numbers and labels and of which:

FIGS. 6A, 6B, 6C: uniform block with retardation time of 1 s; FIGS. 6D, 6E, 6F: uniform block with retardation time of 3 s, FIGS. 6G, 6H, 6I: inclusion Model3-1; and FIGS. 6J, 6K, 6L: inclusion Model1-3.

FIGS. 7A through 7H: SAVE results from a malignant breast lesion. FIG. 7A: normalized applied stress and normalized strain curves from lesion area and surrounding normal tissue, FIG. 7B: B-mode image, FIG. 7C: ROI map for quantification of $E_0$, FIG. 7D: $E_0$ map with boundaries of quantification regions overlaid, FIG. 7E: ROI map for quantification of $E_1$ and $T_1$, FIG. 7F: $E_1$ map with boundaries of quantification regions overlaid, FIG. 7G: $T_1$ map with boundaries of quantification regions overlaid, FIG. 7H: map of fitting error χ.

FIGS. 7I through 7P: SAVE results from a benign breast lesion. FIG. 7J: normalized applied stress and normalized strain curves from lesion area and surrounding normal tissue, FIG. 7I: B-mode image, FIG. 7L: ROI map for quantification of $E_0$, FIG. 7K: $E_0$ map with boundaries of quantification regions overlaid, FIG. 7N: ROI map for quantification of $E_1$ and $T_1$, FIG. 7M: $E_1$ map with boundaries of quantification regions overlaid, FIG. 7O: $T_1$ map with boundaries of quantification regions overlaid, FIG. 7P: map of fitting error $\chi$.

FIG. 8A: p=0.4350; FIG. 8B: p=–4350; FIG. 8C: p=0.1719

FIG. 11 contains Table 1, summarizing all the numerical results from the simulation models.

Figure 1:
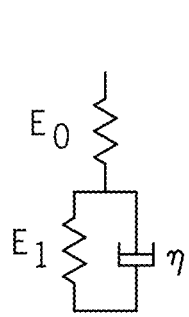
FIG. 1: Standard linear solid model based on first order Kelvin-Voigt element.

The sizes and relative scales of elements in Drawings may be set to be different from actual size and scales to appropriately facilitate simplicity, clarity, and understanding of the Drawings. For the same reason, not all elements present in one Drawing may necessarily be shown and/or labeled in another.

DETAILED DESCRIPTION

This disclosure addresses a methodology of utilization of a custom made proportional-integrator-differentiator (PID)-controlled compression device integrated with an ultrasound imaging system for accurate force application and tracking of the internal deformations in a sample. Simulations evidence that intrinsic viscoelastic parameters cannot be reliably recovered when a 1-D inversion model is used, even in uniform blocks of viscoelastic solids. However, we use the results of the simulation study to highlight the benefits of viscoelastic imaging contrast features as more appropriate measures for lesion differentiation. Based on research, an automated region of interest selection is proposed for calculation of the contrast features based on different viscoelasticity parameters which removes subjectivity in the interpretation of estimated viscoelastic maps in terms of imaging contrast features. The results of use of the proposed approach in a group of breast patients undergoing biopsy are presented and different viscoelasticity parameters are analyzed for significant differences in the two groups of benign and malignant lesions.

Viscoelastic mechanical properties of tissue can be assessed, intrinsically and noninvasively, with the use of the so-called ultrasonic creep test. The ultrasonic creep test methodology includes the ultrasonic application of a step-force to the tissue and ultrasonic monitoring of the local viscoelastic strain response to such force. While so applied, the step-force is used as a stimulus, and the transient strain/stress response (which is governed by viscoelastic properties of the medium) is monitored by recording a sequence of radiofrequency (RF) data (image frames, for example) during the excitation of acoustic radiation force applied to the tissue by ultrasound.

The ultrasonic creep test has two recognized varieties: an internal test and an external test (differentiated from one another based on the type of excitation). In the internal ultrasonic creep test, the acoustic radiation force is employed to apply a step force, inside the medium and to a local portion of it, without any changes in boundary conditions, geometry, or shape while exciting the medium. In the external ultrasonic creep test, a quasi-static stimulus is applied to the entire, overall medium by an ultrasound probe. In this case, the probe motion is driven either manually or automatically for a predetermined time with no contribution of acoustic radiation force. The external ultrasound creep test is more commonly used, and can be considered to be the basis for a specific elastography method used for a study of the viscoelastic properties of the medium—rather than the elasticity of the medium.

Linear Viscoelastic Model (based on conversion of Kelvin-Voigt to Maxwell standard linear solid model)

Figure 2:
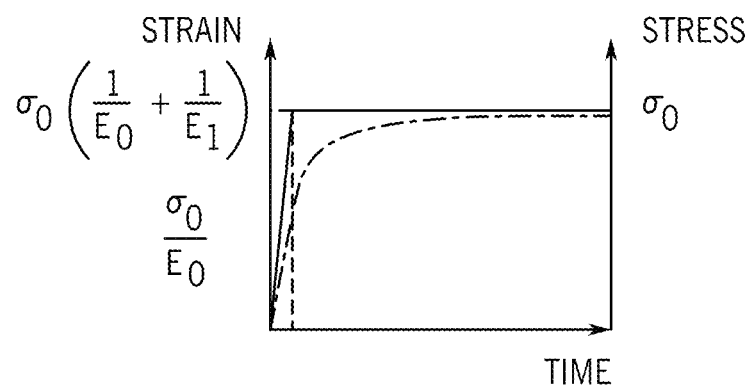
FIG. 2 Model response to a ramp-and-hold input stress. Shaded area represents the mostly elastic part of the strain response.
Figure 10:
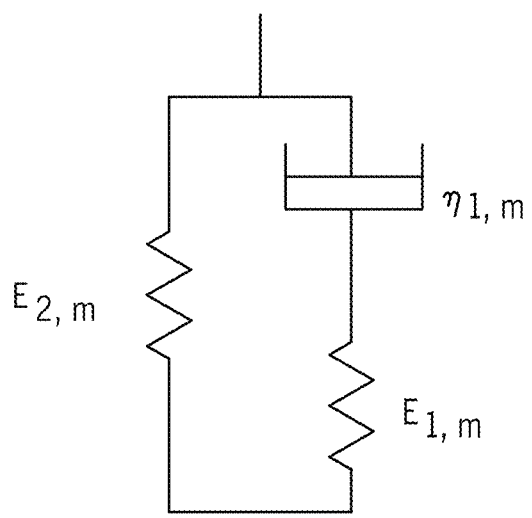
FIG. 10: Representation of a standard linear solid model based on first-order Maxwell element.

Uniaxial creep test is a standard procedure to study long-term viscoelastic properties of materials. In this study, in order to analyze tissue viscoelastic properties, we adopted a standard linear solid model to analyze tissue response under uniaxial creep compression. FIGS. 1, 10 and 2 schematically illustrate a 3-element constitutive model and its stress-strain temporal behavior under a creep test, respectively. According to this model, in response to a ramp-and-hold stress, tissue behaves mostly as an elastic solid during an initial fast compression phase followed by a mostly viscoelastic response.

Hence the parameters of a first order Prony series required for Abaqus simulation can be obtained as $$\tau_1 = \frac{\eta_{1,m}}{E_{1,m}}$$

$$G_0 = \frac{E_{1,m} + E_{2,m}}{2(1+v)}$$

$$g_1 = \frac{E_{1,m}}{E_{1,m} + E_{2,m}}$$

Based on this model, the stress-strain relationship can be formulated as $$\sigma(t) = \begin{cases} \frac{\sigma_0}{T_r} t & t \le T_r \\ \sigma_0 & t > T_r \end{cases} \quad (1)$$

$$\epsilon(t) = \frac{\sigma(t)}{E_0} u(t) + \left(\frac{d}{dt}\sigma(t)\right) * \frac{1}{E_1}\left(1 - e^{-\frac{t}{T_1}}\right) u(t) \approx$$

$$\begin{cases} \frac{\sigma_0}{E_0} \frac{t}{T_r} & t \le T_r \\ \frac{\sigma_0}{E_0} + \frac{\sigma_0}{E_1}\left(1 - e^{-\frac{t}{T_1}}\right) & t > T_r \end{cases}$$

where $\sigma_0$ is the maximum applied stress, $T_r$ is the stress ramp time, u(t) is the Heaviside step function and $T_1 = \eta/E_1$ is the viscoelastic retardation time. Given that $T_r << T_1$, the dashpot shown in FIG. 1(a) does not allow any sudden deformations during ramp time, hence a mostly elastic response is observed due to the spring element in series. The dashpot also does not play any role in the final deformation when time approaches infinity.

In order to define material properties in Abaqus simulation, the constituent model needs to be in the form of a Prony series based on Maxwell standard linear solid model (FIG. 1). However, since parameters of a standard linear solid model based on Kelvin-Voigt model are desired, there is a need in an appropriate conversion. The desired converted parameters can be obtained by equating the creep-compliance response of the two models. By doing so, the parameters of a Maxwell equivalent of the model shown in FIGS. 1, 2 can be found as $$E_{2,m} = \frac{1}{(1/E_0 + 1/E_1)}$$

-continued $$E_{1,m} = E_{2,m} E_0 / E_1$$

$$\eta_{1,m} = \frac{\eta}{E} \frac{1}{(1/E_{1,m} + 1/E_{2,m})}$$

A. Finite Element Modeling

Eq. 1 describes the deformation, cause by the application of the compression force, of a 1-D element. Characterization of 3-D physical materials using this model requires complete knowledge about deformations in all directions. However, ultrasonic tracking of the tissue deformations only provides strain data in one imaging plane (which is mostly accurate along the transducer transmission axis). Hence, to examine the amount of error incurred when using the 1-D model in Eq. 1 for heterogeneous 3-D materials (which is also suitable for studying breast masses), a finite element numerical simulation was performed. Two sets of simulations were considered. In one set of simulations, two uniform blocks of viscoelastic materials with different parameters were analyzed under uniaxial creep with a ramp-and-hold surface stress. The viscoelastic parameters of these materials were chosen such that their combinations present viscoelastic values and contrast features similar to those reported in the previous studies of human breast (such as, for example, by Y. Qiu et a. in *Academic Radiology*, vol. 15, pp. 1526-1533, 2008).

Using the model shown in FIG. 1, ($E_0$=45 kPa, $E_1$=450, $\eta$=450 kPa·s) were selected for material 1, and ($E_0$=45 kPa, $E_1$=450, $\eta$=1350 kPa·s) were selected for material 2. Hence, the two materials 1 and 2 had the same elastic parameters but different viscosity. This resulted in retardation times of 1 s and 3 s for material 1 and 2, respectively.

In another set of simulations, a cylindrical inclusion with diameter of 1 cm from one material was inserted in the other material to mimic a breast tumor. Both material 1 and material 2 were used as inclusions embedded in the other material. The model that had the material with retardation time of 1 s embedded in the material with retardation time of 3 s was referred to as "Model1-3", while the model that had the material with retardation time of 3 s embedded in the material with retardation time of 1 s was referred to as "Model3-1".

In order to mimic the loading asymmetry condition which might occur in realistic in vivo situations, the cylindrical inclusion was shifted up 6 mm from the center of the cube and moved 1 mm to the right side of the cubic background.

In all examples, the bottom of the cube had a tie condition and a slippery condition was considered for interaction of the top surface and the compression plate. The compression plate was assigned a surface area of 6 cm×4 cm, similar to the one used in the in vivo studies, and its center was aligned with the center of the cubic block.

In each simulation, a ramp-and-hold force with a ramp time of $T_r$=0.25 s and final force value of 2N was applied. Nodal axial strain data obtained from each simulation were fitted to the viscoelastic response in Eq 1 in two steps. In the first step, the strain amplitude after 0.25 s was used to estimate $E_0$ based on the Eq (1) for $t \leq T_r$. The initial 0.25 s of the strain data was then removed and a single exponential viscoelastic response (Eq (1); $t > T_r$) was fitted to the remaining of the strain curves to obtain $E_1$ and $T_1$ using Marquette-Leveque nonlinear least square fitting in MATLAB.

B. Force Application and Ultrasonic Displacement/Strain Tracking

Figure 3A:
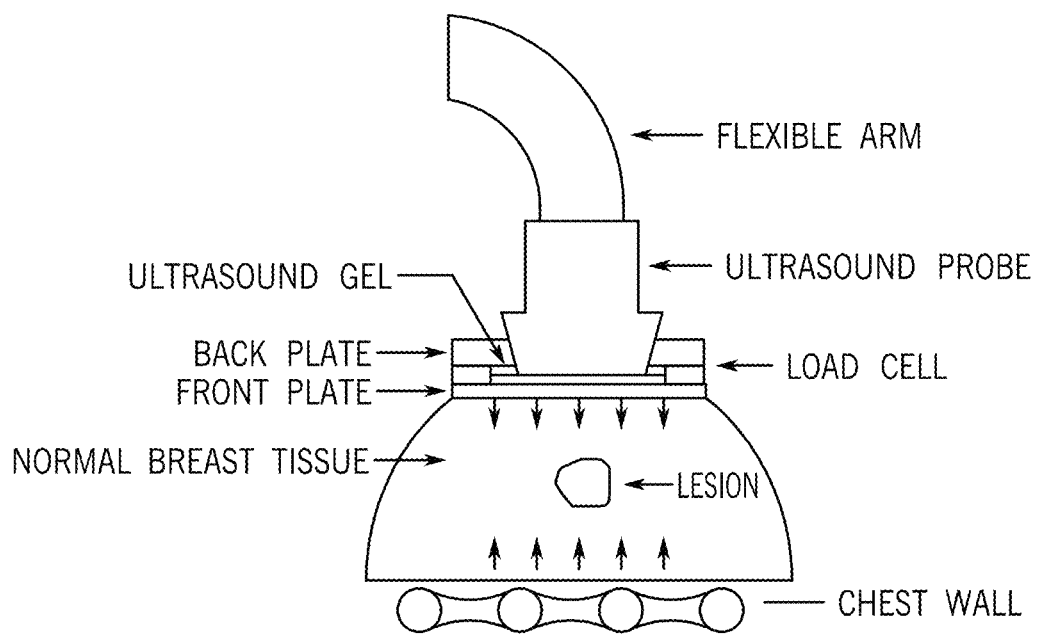
FIGS. 3A, 3B: Schematic diagrams of the uniaxial creep test setup for in vivo viscoelasticity imaging of breast lesions. (an automated compression device employed for measurements/creep test).
Figure 3B:
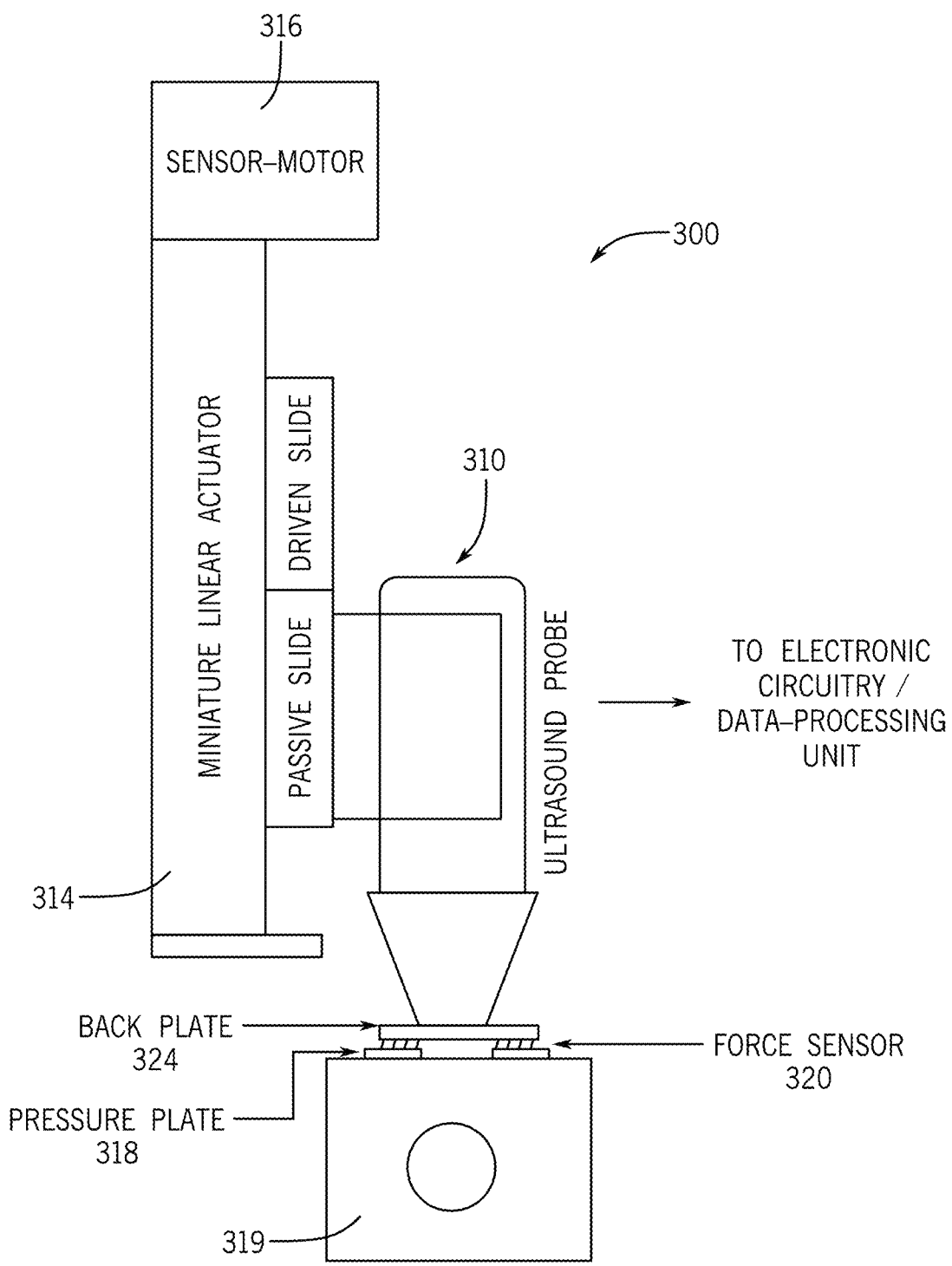

The compression setup schematically presented in FIGS. 3A, 3B was employed to create uniform axial force (on in vivo breast tissue) as well as to acquire ultrasonic radiofrequency data. The ultrasound probe surface was extended via an extension plate composed of a back plate and a front plate.

While the back plate of the set-up was fixed, the front plate was kept in minimal contact with the load cells and was configured to move axially. The edges around two plates were open to allow free motion of the ultrasound gel during the tissue compression. Four load cells were mounted at each corner of the extension plate (between the two plates) for simultaneous measurement and control of the desired force profile.

In particular, as shown in FIG. 3B, the embodiment 300 was equipped with an ultrasound probe 310, which was configured to record local deformation of target (tissue) under stress. This device included a lightweight, miniature linear actuator 1714 (in one implementation—MR20LS with 2 mm lead screw, PBC Linear, Roscoe, Ill.), driven by a brushless DC (BLDC) servomotor 1716, (RP17M brushless DC servomotor with encoder, Electrocraft, Dover, N.H.), which in operation moved a commercial ultrasound probe 310 together with a pressure plate 318 rapidly onto the material or tissue 319 until a preset force level on the probe face was reached. In one implementation, the actuator control system used 4 small load sensors 1720 (FSS015, 15 Newton range, Honeywell, Bloomington, Minn.), embedded in a back plate, to measure the applied force. The control system maintains the preset force level constant for a predetermined period of time (typically about 10-100 seconds). When the creep measurement was complete, the actuator 314 automatically retracted the probe.

Figure 3C:
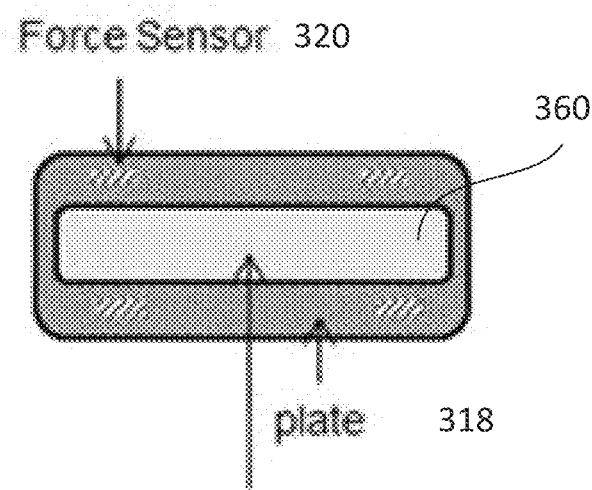
FIG. 3C: spatial coordination of the surface of the probe of FIG. 3B and the pressure plate as well as 4 force sensors positioned at the 4 corners of the pressure plate; in front view; includes the pressure plate with membrane. The load cells are located between the pressure plate and the back plate (not shown in FIG. 3C).

The back plate 324 was custom fit to the probe 310 using a liquid castable plastic material (such as, for example, SmoothCast 300, Smooth-on, Inc., Easton, Pa.). The four small load sensors 320 were sandwiched between the back plate and the pressure plate. FIG. 3C illustrates the position of the load sensors 320 at the 4 corners of the pressure plate 318. Consequently, as the motor of the system keeps compressing the object (target), the resulting resisting force from the object were transferred to the load sensors 320 through the pressure plate 318. There was (an optionally approximately rectangular) opening 360 at the center of both pressure and back plates dimensioned to allow the face of the probe 310 to move though the plate(s) such that the probe face stays at the same level as the pressure plate 318. This opening 360 is covered with a thin acoustically-transparent membrane that transmits the ultrasound beams.

As shown, the four load sensors 320 were symmetrically located at the four corners of the plates 318, 324. The total force was then calculated, with the use of the operably-cooperated with the system 300 programmable computer processor, by averaging the outputs of the sensors 320. The solid pressure plate 318 transferred pressure from the medium/target/tissue to the load sensors 320. Non-uniform contact between the pressure plate and the medium/target may result in unequal loading on the sensors. However, because the outputs of the sensors are averaged, the total output will still correspond to the total force applied to the medium. The overall dimensions of the device, in one embodiment, is 31 cm×7 cm×5.5 cm (length×width×depth).

Figure 4:
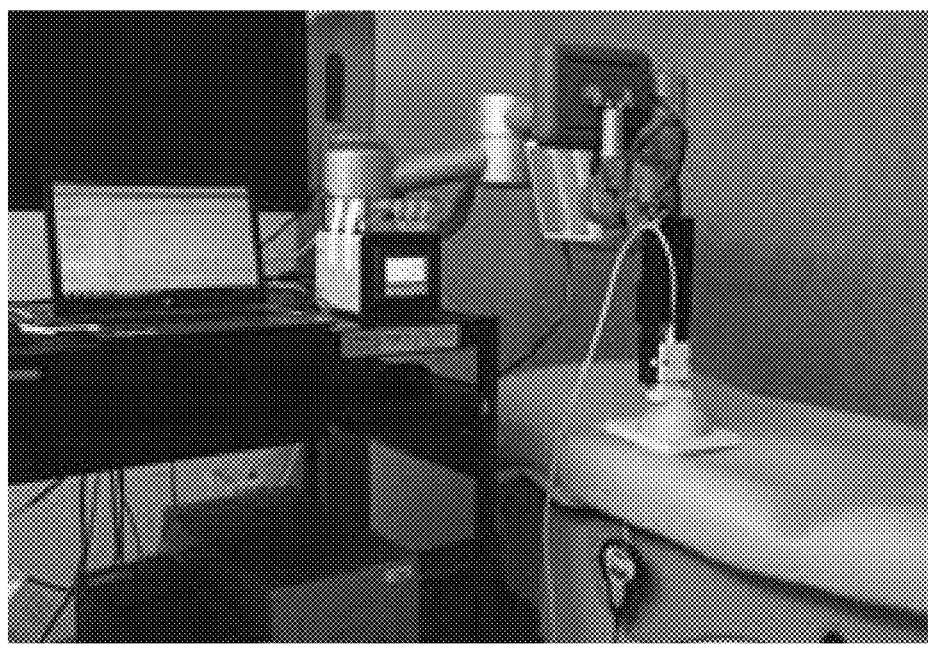
FIG. 4: An image of a set-up, in which a compression device is mounted on a lockable flexible arm. The setup is positioned on a breast elasticity phantom to demonstrate the utility of the device for in vivo studies.

The entire compression setup had portable weight and was mounted on a lockable flexible arm during patient studies (FIG. 4). In order to mimic step-like stress stimulation a fast ramp force is required. Such fast deformation of tissue, if not imaged at appropriate frame rate, can cause severe decorrelation of the axial data which in turn can lead to speckle tracking failure. In order to image all phases of deformation, plane wave imaging was used to acquire raw radiofrequency data at 200 frames per second using a Verasonics programmable ultrasound machine (Verasonics Inc., Kirkland, Wash.) and a linear array transducer L11-4v (Verasonics Inc., Kirkland, Wash.). A two dimensional autocorrelation technique was used for displacement tracking. The fast axis windows length was $3\lambda$ ($\lambda$ is the imaging wavelength at 6.25 MHz with sound speed of 1540 m/s). The slow axis window was 15 ms. The displacement data was then used to estimate induced strain for each pixel in the imaging plane using the staggered strain estimated method in with a window length of $20\lambda$. The resulted strain field was post processed using a $9\lambda \times 9\lambda$ median filter.

C. In Vivo Patient Studies

Data collected from imaging of the breast tissue were analyzed. During the study patients were in a supine position. The compression/imaging setup (FIG. 4) was then positioned on the patient's breast. An experienced sonographer found the lesion and positioned the compression device at each acquisition. Prior to each data acquisition, test compressions were applied to ensure minimal lateral and out-of-plane tissue motions will occur during the actual test. Depending on the location of the lesion, patients were instructed to slightly reposition in order to make best use of the chest wall as a supporting structure for uniform axial compression as is schematically shown in FIG. 3A. A total of 10 seconds of data was collected from each patient at 200 frames per seconds imaging rate. During this time, patients were asked to hold their breath to minimize respiration induced strain artifacts. For each patient a ramp-and-hold force profile was applied with a final force value of 2 N and ramp speed of 8 N/s. This amount of force created a final stress value of $\sigma_0 = 833.33$ Pa, given the compression plate surface of 24 cm$^2$, which ensured linear tissue response based on previous studies. The pre-compression was maintained less than about 0.3 N to avoid any effect due to preloading. The ultrasound strain tracking provided strain curves for each pixel in the imaging domain. Due to variations in the breast tissue viscoelasticity in different patients, the force ramp time was expected to be slightly different from the programmed values. Hence, instead of 0.25 s, is of the initial strain data was omitted to remove the instantaneous elastic response. The remaining viscoelastic compliance curves were fitted to the model in Eq. 1 using Marquette-Leveque nonlinear least square fitting in MATLAB in which complete two dimensional maps of different parameters were created. For each pixel in the imaging plane located at a grid point (m, n), the viscoelastic parameters $E_0$, $E_1$ (with $T_1$ being a retardation time) were estimated as $$\hat{E}_0(m, n) = \frac{\sigma_0}{\epsilon_{m,n}(T_r)} \quad (2)$$

$$(\hat{E}_1(m, n), \hat{T}_1(m, n)) = \underset{(E_1, T_1)}{\operatorname{argmin}} \left\| \frac{\sigma_0}{E_1}\left(1 - e^{-\frac{t}{T_1}}\right) - (\epsilon_{m,n}(t) - \epsilon_{m,n}(T_r)) \right\|^2, t > T_r$$

A normalized fitting residue was calculated for each pixel located at axial-lateral gird point (m, n) in the imaging plane as $$e(m, n) = \frac{\|\epsilon_{m,n}(t) - \hat{\epsilon}_{m,n}(t)\|}{\|\epsilon_{m,n}(t)\|} \quad (3)$$

where $\epsilon_{m,n}(t)$ and $\hat{\epsilon}_{m,n}(t)$ are the measured and fitted strain profiles respectively and $\|.\|$ indicates the Euclidian norm. This measure can be regarded as a parameter for assessing goodness of the fitted viscoelastic model. The residual term in (5) incorporates both slow deviations from the model (e.g. due to a wrong model) as well as strain variations due to inability of the force control in removing fast fluctuations (e.g. due to natural motions such as cardiac motions). The latter appears as zero mean high frequency fluctuations on the strain curves with a minor effect on the estimated parameters of viscoelasticity. Hence the residual term is rescaled based on its energy contained in the frequency range expected for the slow creep response (i.e. <1 Hz). The band-limited fitting residue is considered as the fitting error throughout the rest of the paper.

D. Region of Interest (ROI) Definition

The results of nonlinear fitting process are two dimensional maps of viscoelasticity parameters $E_0$, $E_1$ and $T_1$. The main assumption is that lesions present viscoelasticity features which are different from those of the normal surrounding breast tissue. In practice, however, this difference may not clearly delineate the lesion boundary in the acquired viscoelasticity maps, or different parameters may show different contrast features. In order to make assessment of the tumor margins and background normal tissue less subjective, an automatic method was devised. This method includes the following steps:

1) Initial Seeding of Lesion Boundary

Prior to any compression, lesion boundary was defined from the first B-mode image in the imaging sequence. The speckle tracking displacement data was then used to deform this pre-compressed boundary according to the motion of each point in the imaging plane. The boundary deformation is stopped just before the creep response starts. This deformed boundary is then used for all subsequent analysis of the estimated viscoelastic parameters based on the reduced strain data (the strain data after 1 s).

2) ROI Formation for Measurement of Contrast Values

Figure 5:
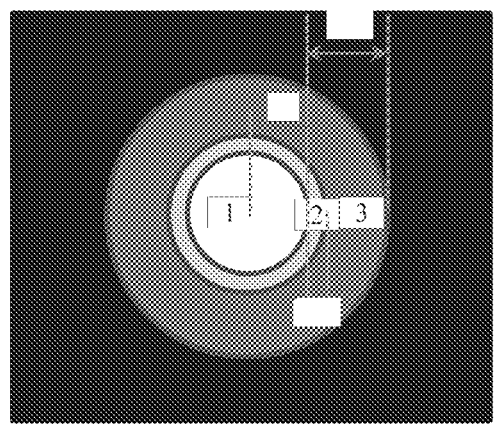
FIG. 5: A schematic diagram illustrating the automated ROI selection based on lesion geometry and morphology dilation. Area 1 represents the lesion and is formed based on the lesion appearance on the B-mode image and continuous tracking of the boundary during deformations. This area is used for quantification of the lesion viscoelastic properties. Area 2 is the results of dilating area 1 and subtracting it. This area is excluded from any quantification due to uncertainty in the lesion size obtained from the B-mode images. Following similar procedure, area 3 is formed and used for quantification of the viscoelastic properties of the normal breast tissue.

To limit the quantification of viscoelastic parameters to lesions area and its surrounding tissues, the deformed lesion boundary explained in the previous section was used to create a region of interest. It is known that in malignant breast lesions, the actual lesion size might be greater than what is observed in B-mode images. Hence, in order to reduce ambiguity in classification of the lesion and normal tissue, a blank quantification mask around the lesion area was established. This mask was created using a dilation operation on the lesion boundary. The dilation was performed using morphological operation to select ROI regions which adapt to the shape and location of different lesions. The dilation size can vary, however, here a dilation factor of 0.3 was empirically chosen for the in vivo data based on the results of lesion size changes reported for the strain elastograms compared to B-mode. A second ROI was then formed using a dilation factor of 1.3 to create and circumscribe an annular area in the surrounding normal tissue with a radius equal to that of tumor radius. As shown in FIG. 5, area 2 is excluded from ant quantification and area 1 and 3 area used for quantification of the lesion and background normal tissue viscoelastic parameters. In case of elongated lesions, the radius along the largest axis was considered.

3) Contrast Values Instead of Intrinsic Parameters

The estimated viscoelasticity parameters based on direction inversion of the 1-D strain data (as demonstrated in the results section) present strong sensitivity to the boundary conditions and geometries. The situation may be even more challenging for in vivo scenarios due to natural heterogeneity of breast tissue and surrounding anatomies. Hence, addition of contrast measures based on viscoelastic parameters may provide a systemic way to reduce these sensitives due to inherent normalization. In this study, for viscoelastic parameter X measured on lesion and background normal tissue, a contrast is defined as $$X \text{ Contrast} = \frac{(X_{lesion} - X_{normal})}{(X_{lesion} + X_{normal})/2} \quad (4)$$

Hence, values of contrast provide a differentiating factor where patient's own normal tissue can be considered as the control observation.

E. Simulation Results

FIGS. 6A, 6B, 6C, 6D, 6E, 6F, 6G, 6H, 6I, 6J, 6K, 6L summarize results of the finite element modeling of the subject of interest. Each sub-combination of three images (for example, the combination of FIGS. 6A, 6B, and 6C) presents a spatial distribution of different viscoelasticity parameters estimated using axial strain data only along with normalized fitting error. The first two sets (FIGS. 6A-6C and 6D-6F) are derived from the uniform blocks with retardation times of 1 s and 3 s, respectively. The second two sets (FIGS. 6G-6I and 6J-6L) represent the results of the inclusion model, where inclusion had a retardation time of 3 s (1 s) and background had a retardation time of 1 s (3 s), respectively.

Figure 6A:
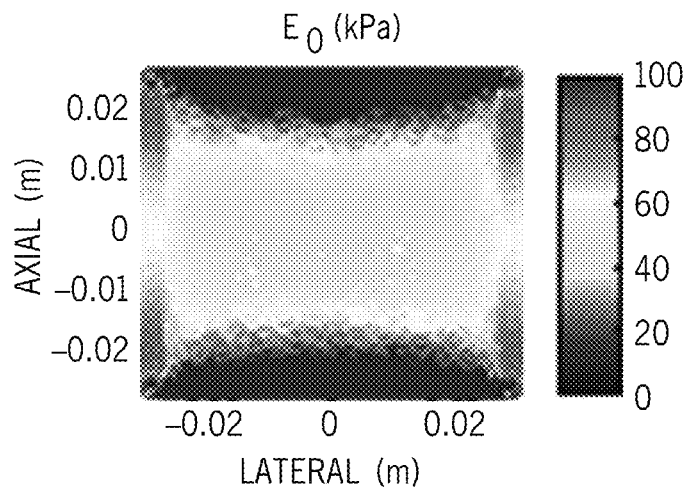
FIGS. 6A through 6L: Examples of two-dimensional maps of viscoelasticity parameters based on direct inversion of the 1-D strain data.
Figure 6B:
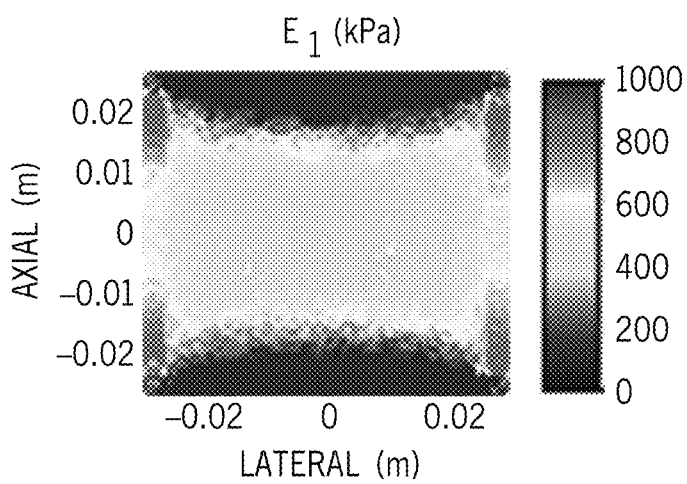
Figure 6C:
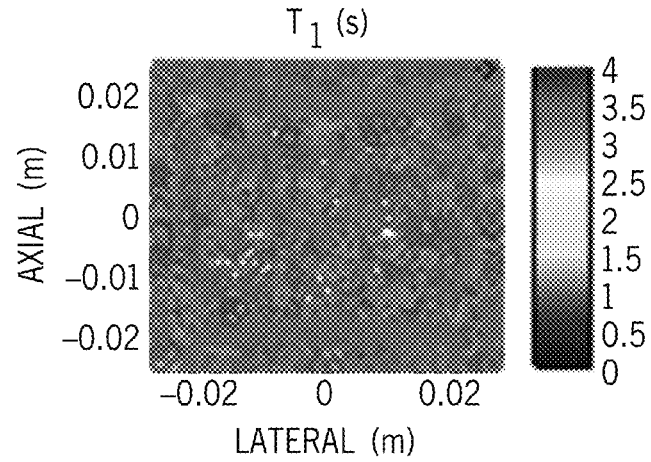
Figure 6D:
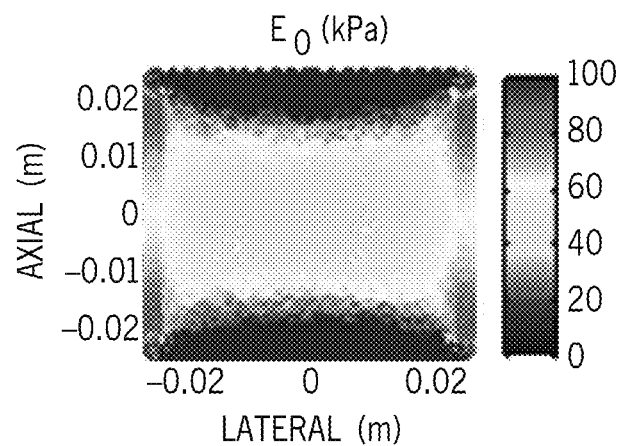
Figure 6E:
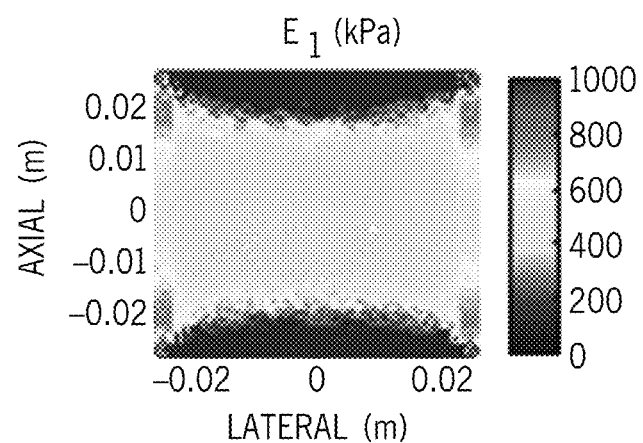
Figure 6F:
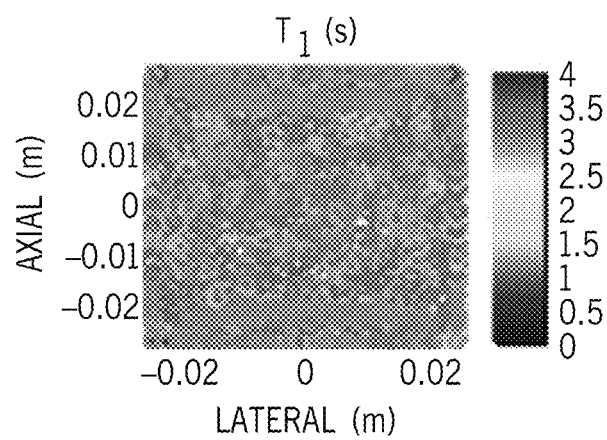
Figure 6G:
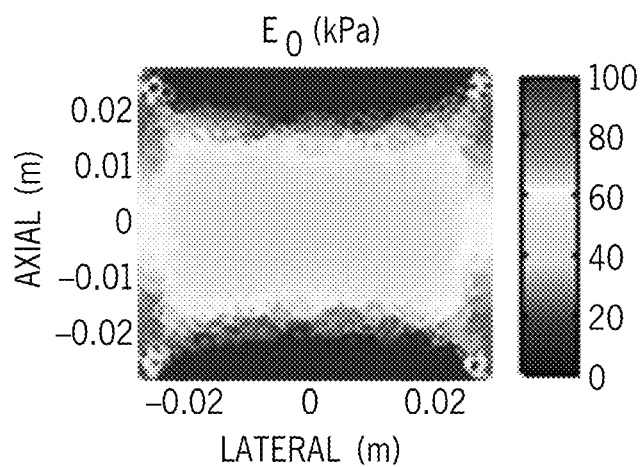
Figure 6H:
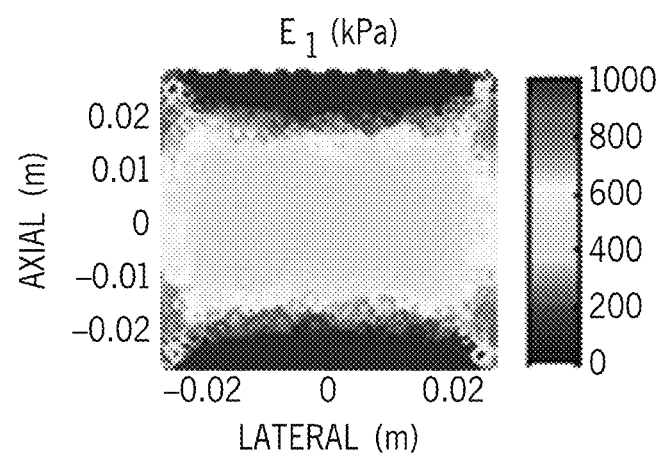
Figure 6I:
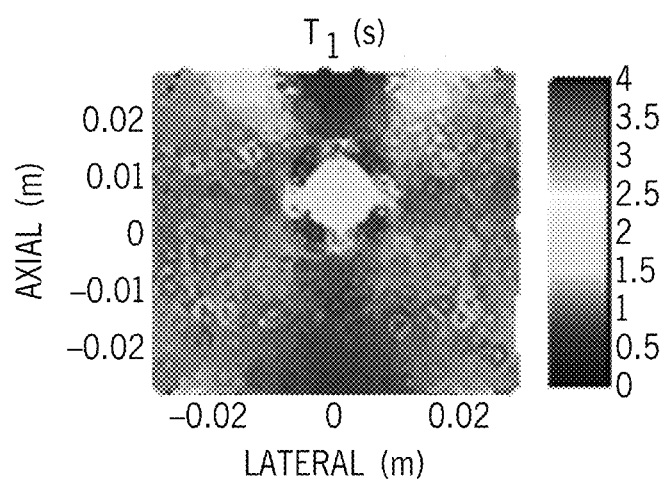
Figure 6J:
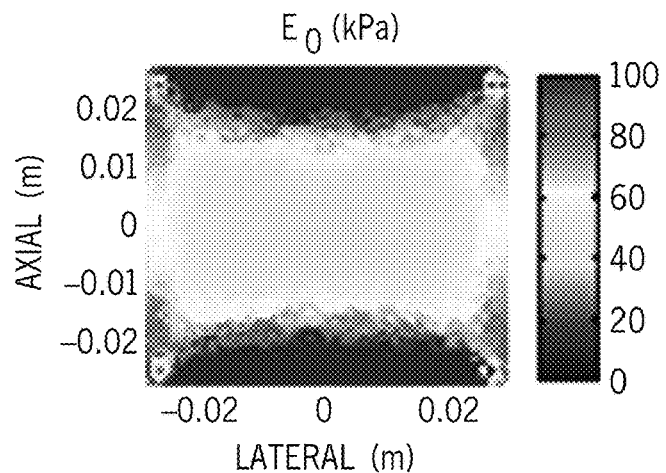
Figure 6K:
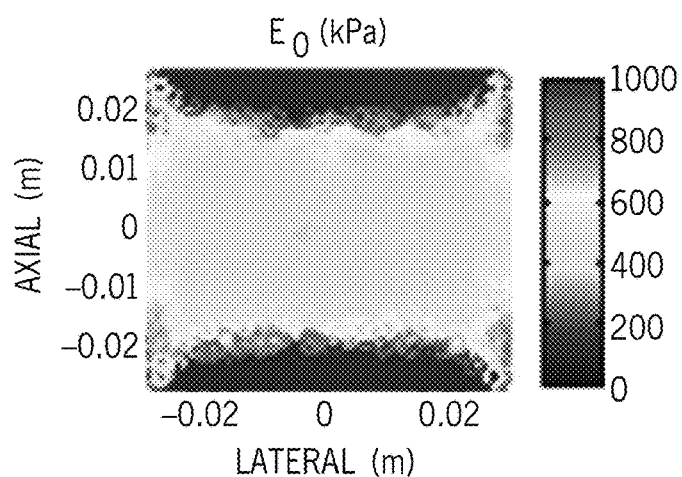
Figure 6L:
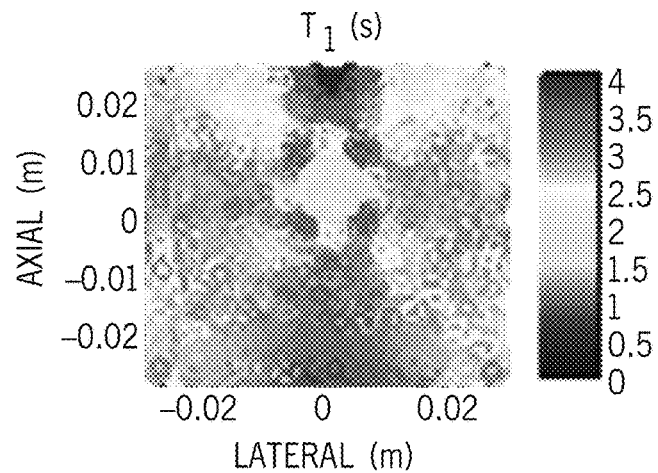

As it can be seen in all cases (FIGS. 6A, 6B, 6D, 6E, 6G, 6H, 6J, 6K), the inversion method shows high degree of error in estimation of the $E_0$ and $E_1$ near the top and bottom surfaces. The estimated values, however, approach the true values near the center of the model. Unlike elastic parameters, retardation time maps do not present noticeable sensitivity to boundary effects in the uniform block models (FIGS. 6 C and 6G), where average estimated $T_1$ values are very close to the input values (less than 1% error in both materials) (FIGS. 6C, 6F). In the inclusion models, however, the estimated $T_1$ maps present spatial variations which can be related to the interaction of different dynamics experienced in the inclusion and background materials during compressional creep force. These interactions are such that, the estimated $T_1$ values from background and inclusion approach each other's value, which in turn, results in a loss of contrast as seen in FIGS. 6I, 6L.

Table 1 (presented as FIG. 11) summarizes all the numerical results from the simulation models. In obtaining these values, in order to avoid any estimation bias due to increased node density near edges (as usually occur in finite element meshing), the viscoelastic parameters estimated from each node's strain data were spatially interpolated to a uniform rectangular grid. Additionally, due to remove rapid fluctuations, 25% of the data residing outside the median values were excluded from the averaging and calculation of the standard deviations. As it can be seen in Table 1, in case of the uniform blocks, while there is a significant bias in the estimation of $E_0$ and $E_1$ (more than 100% for $E_0$ and more than 19% for $E_1$), the estimated viscoelastic retardation times are within the 99% values of the input values for both materials. However, the estimated viscoelastic retardation time in the inclusion models show significant changes. In Model3-1, the inclusion retardation time decreases from 3 s to 1.77 s (more than 40% bias) while it increases from is to 1.1 s (10% bias) in the background. Similarly, in Model1-3, the inclusion retardation time increases from is to 2.16 s (116% bias), while it decreases from 3 s to 2.91 s (3% bias) in the background. In both inclusion models, while the background elastic parameters $E_0$ and $E_1$ present significant bias (more than 44% for $E_0$ and more than 24% for $E_1$), the inclusion elastic parameters $E_0$ and $E_1$ are in strong agreement with the input values (less than 10% bias for $E_0$ and less than 3% bias for $E_1$).

F. In Vivo Study Results Reconstruction Examples

Figure 7A:
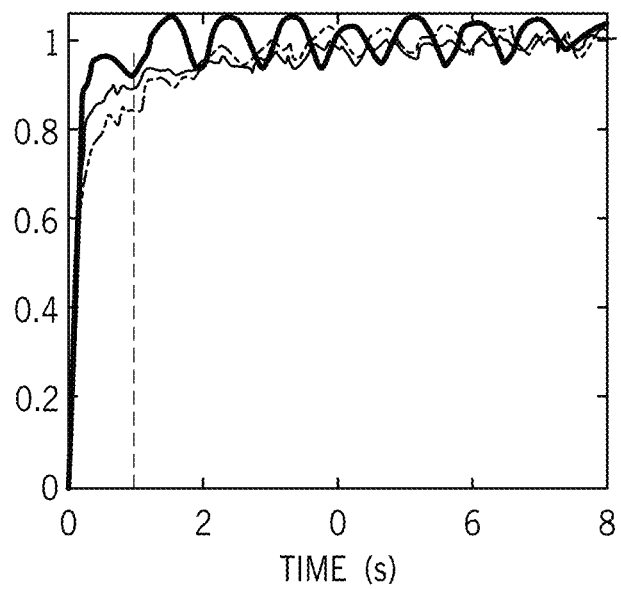
Figure 7B:
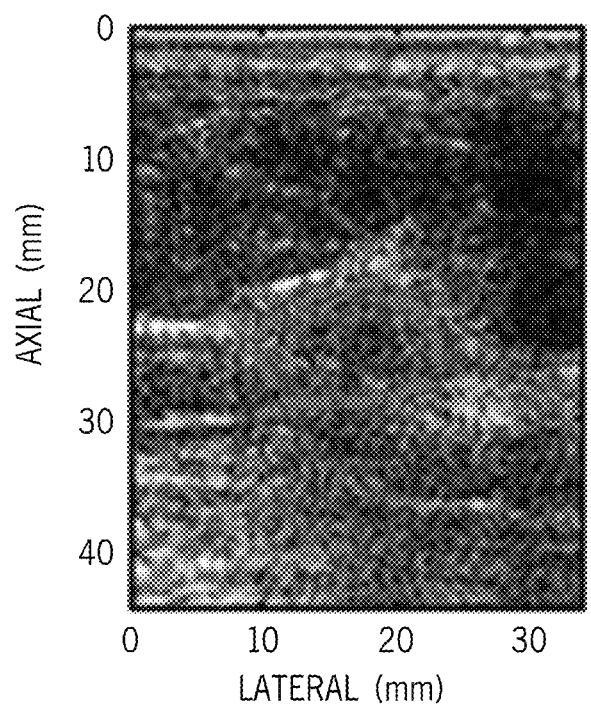
Figure 7C:
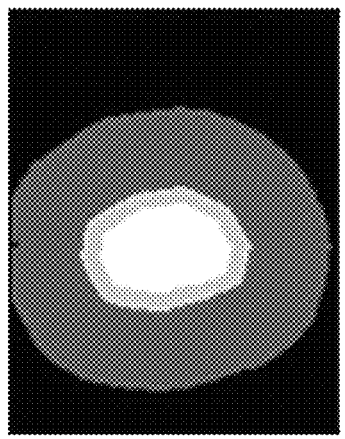
Figure 7D:
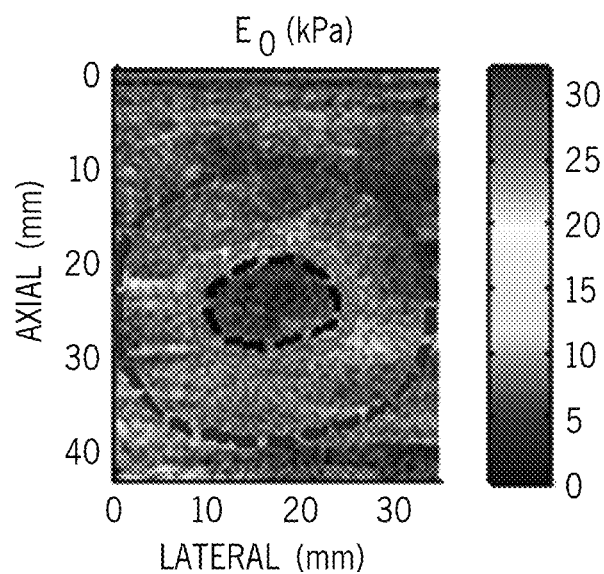
Figure 7E:
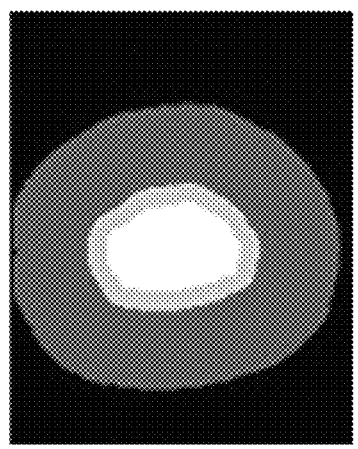
Figure 7F:
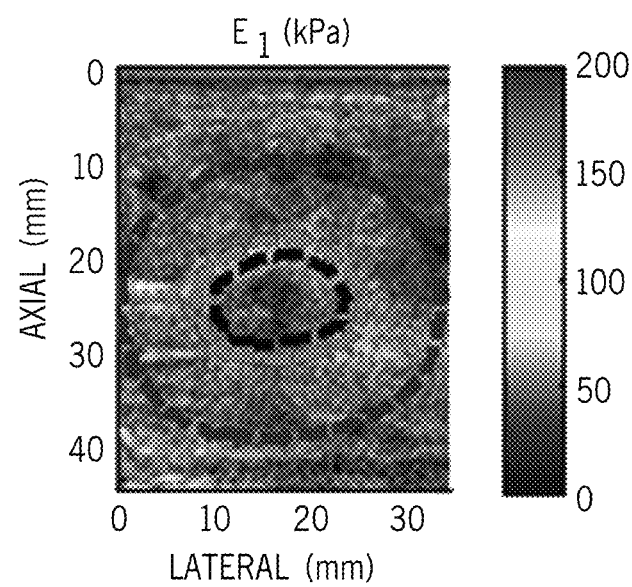
Figure 7O:
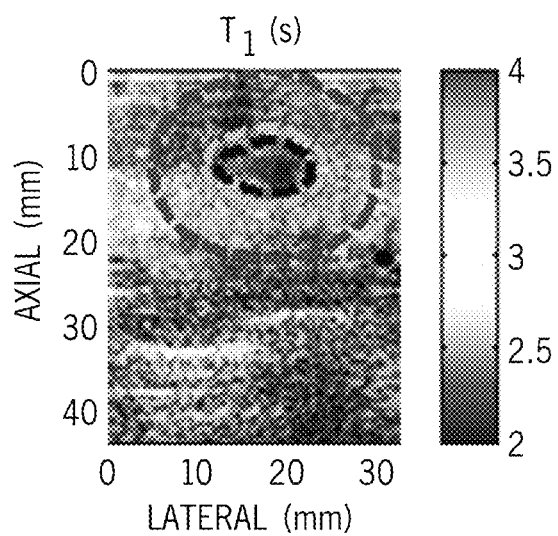
Figure 7P:
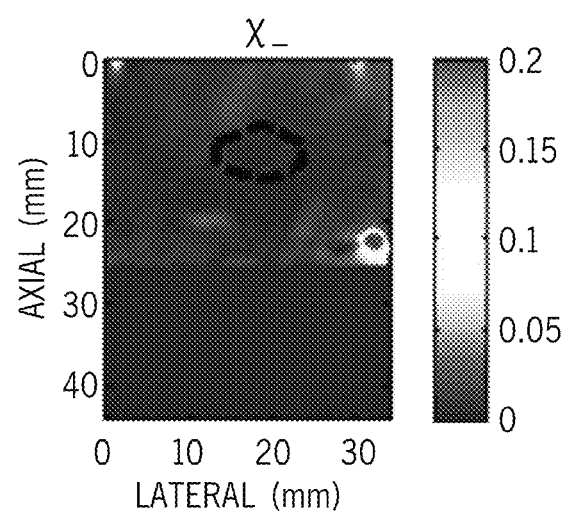

Images of FIGS. 7A through 7P summarize the results of SAVE on two subjects, one with a malignant invasive carcinoma and another with a benign fibroadenoma. In each case, lesion boundary is highlighted using a red dashed line in the B-mode image and dashed red line in the corresponding maps of different viscoelasticity parameters. Using the ROI selection criteria explained in the previous section, lesion area, a quantification mask area and normal tissue area are defined. These quantification areas are defined for both initial elastic response (FIGS. 7C, 7L) and viscoelastic response (FIGS. 7E, 7N). The colored areas highlighting different quantification regions are similar to those in FIG. 5 where in each viscoelasticity map the magenta and blue dashed lines highlight the boundary of region 2 and 3 respectively. FIGS. 7A, 7J show the normalized surface stress and representative normalized strain time curves from the lesion area and normal surrounding tissue. As it can be seen in both cases, the strain response comprises of an initial fast elastic response followed by a slow viscoelastic response. The vertical dashed blue lines in the graphs indicate the time boundary that separates the mostly elastic response from mostly viscoelastic. In both cases, the stress time curves present cyclic fluctuations which can be attributed to the cardiac-induced stress not completely removed due to the wide bandwidth of the force-control feedback loop. This wide bandwidth was essential to be able to provide fast force ramps to better mimic a creep tests. Similar to the simulation models, the estimated $E_0$ and $E_1$ maps show significant overestimation near the skin as can be seen in FIGS. 7D, 7F, 7K, 7M. In the case of malignant lesion (FIGS. 7A through 7H), a clear contrast can be seen in all viscoelasticity parameters $E_0$, $E_1$ and $T_1$ which corroborate with the lesion boundary obtained from the B-mode images. The elasticity maps $E_0$ and $E_1$ present a positive contrast in the lesion area which indicate higher stiffness of the lesion compared to the background tissue. The viscoelasticity retardation time maps, $T_1$, on the other hand presents a negative contrast, indicating a faster creep response in the lesion area compared to the surrounding tissue. In the case of benign lesion (FIGS. 7I through 7P), while no significant contrast is observed in the maps of elasticity parameters $E_0$ and $E_1$, a distinct positive contrast is seen in the $T_1$ map which is in strong agreement with the appearance of the lesion in the B-mode image in terms of shape and location. FIGS. 7H, 7P show that the normalized root mean square fitting error, $\chi$, is negligible throughout most of the reconstruction maps in both cases. It can be also noted that, in case of the benign lesion, a small area exhibiting more than 20% deviation from the enforced model is excluded from all reconstruction maps. Using the quantification regions shown in FIGS. 7C, 7L, 7E, 7N, for each case, the mean and standard deviation of $E_0$ and $E_1$ and $T_1$ for lesion and background normal tissue were calculated and are shown in Table 2. Additionally, contrast parameters based $E_0$ and $E_1$ and $T_1$ were also found.

Statistical Results

Figure 8A:
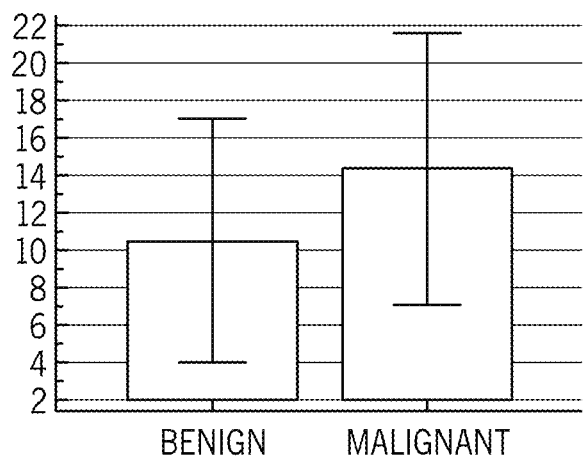
FIGS. 8A, 8B, 8C: Error-bar plots of different viscoelasticity parameters $E_0$ and $E_1$ and $T_1$ in benign and malignant lesions.
Figure 8B:
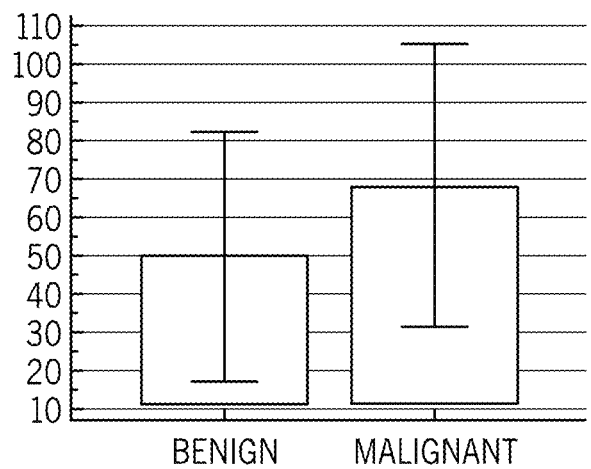
Figure 8C:
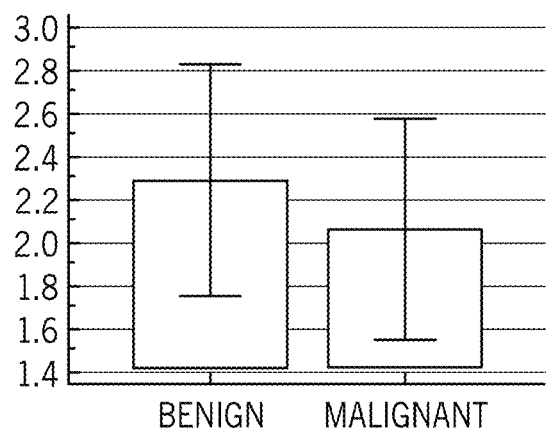

FIGS. 8A, 8B, 8C show the error-bar plot of mean for viscoelasticity parameters $E_0$ and $E_1$ and $T_1$ in the two groups of patients with biopsy-proven benign and malignant lesions. The mean elasticity values $E_0$ and $E_1$ are higher in the group of malignant cases but these differences are not statistically significant (P=0.4350). The mean viscoelastic retardation time $T_1$ is larger in the benign lesions compared to malignant. This difference was not found to be significant P=0.1719.

Figure 9:
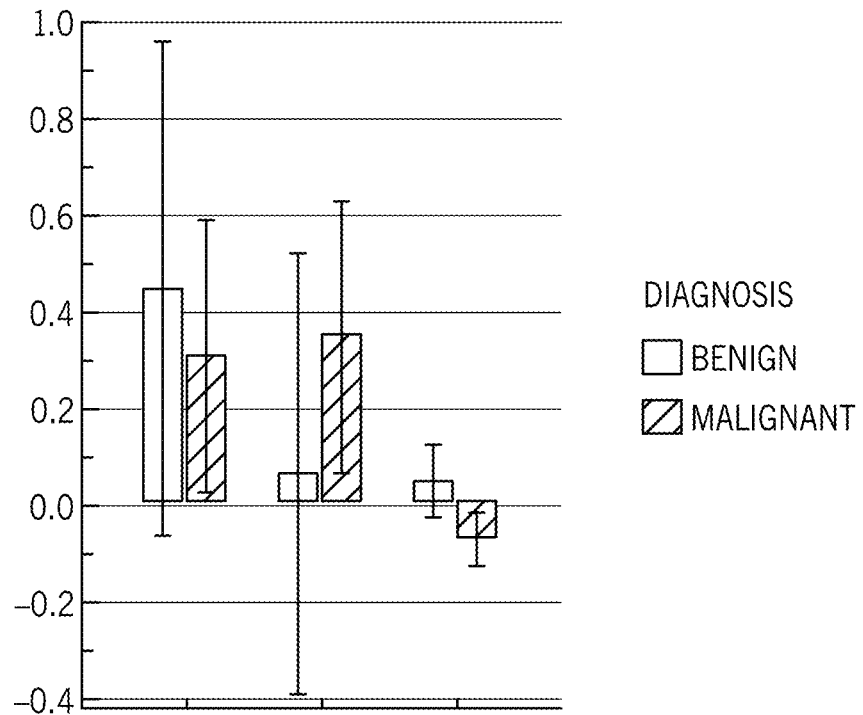
FIG. 9: Error-bar plot representing contrast, determined based on different viscoelasticity parameters in benign and malignant lesions.

FIG. 9 shows the error-bar plot of contrast values based on different viscoelasticity parameters. As it can be seen, while contrast values based on elastic parameters ($E_0$ and $E_1$) do not present a significant difference in the two groups of benign and malignant patients, $T_1$ contrast presents a mostly positive contrast for benign lesions and a negative contrast for malignant cases. The mean $T_1$ contrast was found to be significant in the two groups of patients (P=0.0147).

G. Discussion.

It is appreciated, therefore, that a method for imaging linear viscoelastic properties of breast lesions based on a creep-like test, has been discussed. We presented the results of a finite element simulations as well as in vivo cases when using an automated force ramp-and-hold compression device integrated with a programmable ultrasound machine.

Simulations.

The simulation models were intended to assess different aspects of a creep-like test with uniaxial strain data for retrieving different viscoelasticity parameters. It was shown that the 1-D inverse modelling of the elastic parameters show significant sensitivity near boundaries which results in highly unrealistic moduli of elasticity. The viscoelasticity retardation time, however, was not seen to be sensitive to boundary effects and 1-D inverse modelling on the uniform blocks resulted in accurate and spatially uniform recovery of the retardation times. When testing inclusion models, elasticity parameters presented similar sensitivity issue near boundaries. The viscoelasticity retardation time, though not affected by the boundary conditions, showed spatial variability and bias in both inclusion and background materials. This is an indication that the estimated retardation times from the 1-D model cannot accurately represent intrinsic material parameters. Instead, the estimated parameters should be used solely as imaging contrast features.

Patient Studies

We presented SAVE reconstruction maps from two breast patients. In order to interpret different viscoelasticity parameters in terms of values and contrast values, definition of an ROI is necessary to separate the parameters of lesion from those of background tissue. ROI selection has been a major obstacle in objective interpretation and quantification of the mechanical properties acquired by different elastography methods. This is especially important as lesion B-mode features (e.g. size) do not always coincide with the features seen in the maps acquired from viscoelastic reconstructions. In this paper, we presented a novel ROI selection method based on an initial seeding of the lesion boundary in pre-compressed B-mode images and continuous tracking of this contour through different phases of deformation. This method enabled automatic definition of the quantification regions and exclusion of the regions where lesion-background margin cannot be reliably estimated from the B-mode images. In case of the malignant lesion, the estimated lesion boundary derived from the B-mode image favorably coincided with the margin of an area with elevated $E_0$ and $E_1$ values and decreased $T_1$. In case of the being lesion, only $T_1$ map presented a noticeable contrast with distinct margins that corroborated with the automatic ROI boundaries derived from the B-mode image. In both cases, very low values of fitting errors ensured the suitability of the standard linear solid model based on a first order Kelvin-Voigt model.

The preliminary results of SAVE in 17 patients with breast lesions indicated that malignant lesions had higher elasticity values (both $E_0$ and $E_1$) compared to the benign lesions. Additionally, benign lesions showed larger lesion viscoelastic retardation times compared to the malignant cases. However, none of these findings were statistically significant. Among other factors, the sensitivity of the 1-D inversion on lesion geometry, location and boundary condition (as also observed in the simulations) can greatly limit the ability of this method in resolving intrinsic viscoelasticity values under different conditions which may be experienced during in vivo studies. However, the $T_1$ contrast values were mostly positive in the benign cases and mostly negative in the malignant lesion. The difference in $T_1$ contrast values in the two groups was found to be statistically significant (P=0.0147). Hence, contrast values may provide better discrimination powers due to inherence normalization which is included in calculation of these values (Eq. 4).

In this study an automated method for imaging of the breast lesions viscoelastic properties using a creep-like test was presented. We discussed two dimensional reconstruction maps for different parameters of a linear viscoelastic model. We also described different aspects of this test when performing these tests on live subjects and discussed the suitability of a 1-D inversion model in capturing different viscoelasticity parameters. An automated method for ROI selection was also introduced which was only dependent on the appearance of the breast lesion on pre-compressed B-mode images. Based on this ROI, estimated viscoelasticity parameters, it is possible to calculate contrast values which may help in enhanced differentiation of breast masse. Employing SAVE in a larger group of patient will provide better understanding about variations of different viscoelasticity parameters in different types of breast lesion and finding new biomarkers for enhanced differentiation of benign from malignant cases.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention. In this disclosure, embodiments have been described in a way that enables a clear and concise specification to be written, but it is intended and will be appreciated that elements/components of related embodiments may be variously combined or separated without parting from the scope of the invention. In particular, it will be appreciated that all features described herein are applicable to all aspects of the invention.

In addition, it is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated generally falls under and may vary within a numerical range defined by an experimental measurement error that is typical when using a measurement method accepted in the art for such purposes.

Notably—whether explicitly illustrated in the drawings or not—an embodiment of the reinjection system of the invention includes electronic circuitry (for example, a computer processor) controlled by instructions stored in a memory, to perform specific data collection/processing and calculation steps as disclosed above. The memory may be random access memory (RAM), read-only memory (ROM), flash memory or any other memory, or combination thereof, suitable for storing control software or other instructions and data. Those skilled in the art should would readily appreciate that instructions or programs defining the operation of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement a method of the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

The invention as recited in claims appended to this disclosure is intended to be assessed in light of the disclosure as a whole, including features disclosed in prior art to which reference is made.

Various changes in the details, steps and components that have been described may be made by those skilled in the art within the principles and scope of the invention. For example, the implementation of the real-time control and adjustment of the internal pressure of the adipose tissue during the process of transfer of such tissue through the system can be employed with a syringe-based system with or without the syringe pump (while, for example, affixing the pressure sensor to the tubing transferring the fatty fluid from the syringe to the recipient location to instantaneously measure the pressure as discussed above or via measuring the increase in resistance to the movement of the syringe plunger, and to block the transfer channel from passing the adipose tissue once the pressure exceeds the pre-determined threshold level).

Disclosed aspects, or portions of these aspects, may be combined in ways not listed above. Accordingly, the invention should not be viewed as being limited to the disclosed embodiment(s).

The invention claimed is:

1. A system for ultrasound imaging of a compressed target object, the system comprising:
    a compression device configured
        to apply a compression force to an area of the target object,
        to increase the compression force with a constant ramp time from an initial value to a final predetermined value, and,
        once the final predetermined value has been reached, to maintain said compression force applied to the target object at a substantially constant level;
    an ultrasound probe including an ultrasound transducer, said probe mechanically coupled with the compression device and configured to receive an ultrasound wave from the target object in a time-window during which the compression device holds the ultrasound probe in contact with the target object and while said compression force is being applied to the target object;
    an ultrasound imaging system cooperated with the ultrasound probe and configured to record a sequence of ultrasound image data frames during the time-window, wherein the ultrasound image data frames represent a region of interest (ROI) of said target object;
    a compression device controller, operably cooperated with the compression device and including electronic circuitry that is programmed
        to set and control the ramp time, and
        to synchronize an operation of the compression device with an operation of the ultrasound imaging system; and a data-processing unit configured
- to receive signal outputs produced at least by the ultrasound imaging system and the compression device controller, said signal outputs representing the target object imaged with the ultrasound imaging probe while being compressed by the compression device, and
- to determine, in time domain and based on said signal outputs, a spatial profile of a strain response of the target object to said compression force as a function of (i) time, and (ii) a viscoelastic retardation time characterizing the target object;
- to determine, in time domain, a two-dimensional distribution of first and second viscoelastic parameters characterizing the area, to which said compression force has been applied, based on said spatial profile, according to $$\hat{E}_0(m, n) = \frac{\sigma_0}{\epsilon_{m,n}(T_r)},$$

$$(\hat{E}_1(m, n), \hat{T}_1(m, n)) = \operatorname*{argmin}_{(E_1, T_1)} \left\| \frac{\sigma_0}{E_1}\left(1 - e^{-\frac{t}{T_1}}\right) - (\epsilon_{m,n}(t) - \epsilon_{m,n}(T_r)) \right\|^2, t > T_r$$

wherein $\sigma_0$ is a maximum value of stress caused by the compression force, $T_r$ is the ramp time, $T_1$ is the viscoelastic retardation time, $\epsilon_{m,n}(t)$ and $\hat{\epsilon}_{m,n}(t)$ are a two-dimensional distribution of a measured strain profile and a two-dimensional distribution of a fitted strain profile respectively; and $\|.\|$ indicates the Euclidian norm.

2. The system according to claim 1, wherein the ultrasound imaging system is configured to generate a map, of at least one of a viscoelastic parameter, from the first and second viscoelastic parameters, and the viscoelastic retardation time characterizing the target object, based on results of non-linear fitting of said spatial strain profile and, optionally, to display said map as a color overlay over an image of the target object procured in a B-mode of operation of the ultrasound probe.

3. The system according to claim 1, wherein the ultrasound imaging system is configured to record a sequence of the image frames, each image frame representing a 2D image of the target object.

4. The system according to claim 1, wherein the ultrasound imaging system is configured to record a sequence of the image frames each representing a 3D image of the target object and generate a signal output further used by the data-processing unit to determine a viscoelastic parameter, from the first and second viscoelastic parameters, characterizing said target object.

5. The system according to claim 1, wherein the ultrasound imaging system is configured to record a sequence of the image frames at a rate of hundreds of frames per second while the target object is being insonated with an ultrasound wave shaped as either a substantially plane wave or a spatially-localized beam, wherein a shape of the ultrasound wave is chosen depending on a compression rate of the target object.

* * * * *

UNITED STATES PATENT AND TRADEMARK OFFICE
CERTIFICATE OF CORRECTION

PATENT NO. : 11,234,673 B2  
APPLICATION NO. : 16/167791  
DATED : February 1, 2022  
INVENTOR(S) : Mostafa Fatemi et al.

Page 1 of 1

It is certified that error appears in the above-identified patent and that said Letters Patent is hereby corrected as shown below:

In the Specification

Column 9, Line 41, "is" should be --1s--.

Column 11, Line 63, "is" should be --1s--.

Column 11, Line 65, "is" should be --1s--.

Signed and Sealed this  
Twenty-second Day of March, 2022

Drew Hirshfeld  
*Performing the Functions and Duties of the*  
*Under Secretary of Commerce for Intellectual Property and*  
*Director of the United States Patent and Trademark Office*